(12) United States Patent
Brown et al.

(10) Patent No.: US 9,000,198 B2
(45) Date of Patent: Apr. 7, 2015

(54) MIXED-VALENT TRANSITION METAL-PHOSPHORANIMIDE CATALYSTS

(71) Applicant: Governors of the University of Alberta, Edmonton (CA)

(72) Inventors: Houston J. S. Brown, Edmonton (CA); Jeffrey Mark Stryker, Edmonton (CA); Dominque M. Hebert, Edmonton (CA)

(73) Assignee: Governors of the University of Alberta (CA)

( * ) Notice: Subject to any disclaimer, the term of this patent is extended or adjusted under 35 U.S.C. 154(b) by 142 days.

(21) Appl. No.: 13/899,262

(22) Filed: May 21, 2013

(65) Prior Publication Data

US 2014/0350275 A1 Nov. 27, 2014

(51) Int. Cl.
C07F 19/00 (2006.01)
B01J 31/22 (2006.01)
C07F 9/535 (2006.01)

(52) U.S. Cl.
CPC .............. B01J 31/22 (2013.01); C07F 19/00 (2013.01); C07F 9/5355 (2013.01)

(58) Field of Classification Search
CPC .......... C07F 9/5355; C07F 19/00; B01J 31/22
USPC ........................................................ 556/22
See application file for complete search history.

(56) References Cited

U.S. PATENT DOCUMENTS 6,239,061 B1 5/2001 Wang et al.
6,846,769 B2 1/2005 Arndt-Rosenau et al.

FOREIGN PATENT DOCUMENTS

| CA | 2605077 | 4/2009 |
|---|---|---|
| EP | 0881233 | 12/1998 |
| EP | 0890581 | 1/1999 |
| WO | WO 00/05236 | 2/2000 |
| WO | WO 00/05238 | 2/2000 |
| WO | WO 01/19512 | 3/2001 |
| WO | WO 2009/043156 | 4/2009 |
| WO | WO 2009/043157 | 4/2009 |

OTHER PUBLICATIONS

Camacho-Bunquin et al., Journal of American Chemical Society, vol. 135, pp. 5537-5540 (2013).*
U.S. Appl. No. 13/899,322, filed May 21, 2013, Brown et al.
Chianelli et al., "Unsupported transition metal sulfide catalysts: 100 years of science and application," Catalysis Today, 2009, vol. 147, Iss. 3-4, pp. 275-286.
Dehnicke et al., "Phosphoraneiminato complexes of transition metals," Coordination Chemistry Reviews, 1999, vol. 182, Iss. 1, pp. 19-65.

(Continued)

*Primary Examiner* — Porfirio Nazario Gonzalez
(74) *Attorney, Agent, or Firm* — Sheridan Ross P.C.

(57) ABSTRACT

Phosphoranimide-metal catalysts are disclosed. The catalysts comprise first row transition metals such as nickel, cobalt or iron. The hydrocarbon-soluble catalysts have a metal to anionic phosphoranimide ratio of 1:1, and have no inactive bulk phase and no dative ancillary ligands. The electronic state of the clusters can be adjusted to optimize catalytic activity for a range of commercially important reductive transformations, including hydrodesulfurization. A method of synthesis of these catalysts by anionic metathesis of a halide substituted precursor followed by oxidation is also disclosed.

25 Claims, 3 Drawing Sheets

Structure of [MeCo(NPEt$_3$)]$_4$.

(56) References Cited

OTHER PUBLICATIONS

Duchet et al., "Carbon-Supported Sulfide Catalysts," Journal of Catalysis, 1983, vol. 80, Iss. 2, pp. 386-402.

Evans, "The determination of the paramagnetic susceptibility of substances in solution by nuclear magnetic resonance," Journal of the Chemical Society (Resumed), 1959, pp. 2003-2005.

Guérin et al., "Synthesis, Structure, and Reactivity of the Phosphinimide Complexes (t-Bu$_3$PN)$_n$MX$_{4-n}$ (M = Ti, Zr)," Organometallics, 2000, vol. 19, Iss. 16, pp. 2994-3000.

Klien et al., "Novel Imido- and Phosphorane-Imido-Nickel(II) Complexes. Crystal and Molecular Structure of ($\mu_3$-NH)($\mu_3$-NPMe$_3$)(NiClPMe$_3$)$_3$," Journal of the American Chemical Society, 1991, vol. 113, pp. 4673-4675.

Mast et al., "Vinyl-type polymerization of norbornene by a nickel-based catalyst with phosphoraneiminato ligands," Macromolecular Rapid Communications, 1999, vol. 20, Iss. 4, pp. 232-235.

Ramos et al., "Titanium ferrocenyl-phosphinimide complexes," Dalton Transactions, 2010, vol. 39, Iss. 5, pp. 1328-1338.

Riese et al., Cobalt(II)-organische Phosphaniminato-Komplexe mit Heterocuban-Struktur. Kristallstrukturen von [CoBr(NPR$_3$)]$_4$ mit R = Me, Et, [Co(C≡C—CMe$_3$)(NPMe$_3$)]$_4$ und [Co(C≡C—SiMe$_3$)(NPEt$_3$)]$_4$, Zeitschrift für anorganische und allgemeine Chemie (Journal of Inorganic and General Chemistry), 1998, vol. 624, Iss. 8, pp. 1279-1284.

Schroers et al., "Grafting of Vinyl-Type Polynorbornene on Polybutadiene and Polyisoprene," Macromolecular Chemistry and Physics, 2002, vol. 203, Iss. 18, pp. 2658-2664.

Vissers et al., "The Role of Co in Sulphidised Co—Mo Hydrodesulphurisation Catalysts supported on Carbon and Alumina," Journal of the Chemical Society, Faraday Transactions 1: Physical Chemistry in Condensed Phases, 1987, vol. 83, Iss. 7, pp. 2145-2155.

Yadav et al., "Phosphinimide complexes with pendant hemilabile donors: synthesis, structure and ethylene polymerization activity," Dalton Transactions, 2009, Iss. 9, pp. 1636-1643.

\* cited by examiner

Structure of [MeCo(NPEt$_3$)]$_4$.

Structure of [MeCo(NPEt₃)]₄PF₆.

Structure of [Fe(NP'Bu₃)Br]₂.

MIXED-VALENT TRANSITION METAL-PHOSPHORANIMIDE CATALYSTS

FIELD

This disclosure relates to phosphoranimide-transition metal catalysts, the synthesis of these catalysts, and the use of these catalysts for reductive reaction processes, such as hydrodesulfurization and hydrogenation.

BACKGROUND

A range of industrial-scale chemical processes use catalysts for the reduction of organic compounds and feedstocks. Many industrial catalysts are transition metal catalysts. Second and third row transition metals are most frequently associated with high reactivity, but the high cost, scarcity, and toxicity of precious and semi-precious metals raise barriers to economically- and environmentally-sustainable large-scale chemical processes. The late first row transition metals (e.g. cobalt, nickel, iron, copper, etc.), also termed "base metals" are relatively inexpensive, abundant, and often less toxic than the heavier metals. However, base metals in general display inherently low reactivity and limited scope, features attributable in part to the small size of these elements. Nonetheless, the base metals are attractive candidates for use in catalysis, provided a suitable metal core and coordination environment can be identified.

Catalytic reduction of organic compounds is a key enabling process that sustains several major chemical industries. A broad range of commercially important reductive transformations are catalyzed by transition metals. For example, the transition-metal catalyzed reductive cleavage of polar bonds, such as C—S and C—N bonds, and hydrogenation of unsaturated functional groups, such as alkenes (to alkanes), are reductive transformations pertinent to the production of environmentally safe fuels from crude petroleum feedstocks and to the production of fine chemicals.

Current industrial processes that utilize catalytic reduction are commonly mediated by relatively expensive, relatively rare, and in some cases toxic second- and third-row transition metals. The use of rare and precious transition metals raises barriers to the economic and environmental sustainability of these industrial processes. As an example, current technologies for the upgrading of petroleum feedstocks, which include hydrodesulfurization (HDS) and hydrodenitrogenation (HDN), are energy intensive. This is due to the harsh reaction conditions required for the metal catalysts currently used for these large-scale upgrading processes. Molybdenum and tungsten catalysts, promoted by cobalt and nickel ions, such as $CoMoS_2$ and $NiWS_2$, generally function only at high temperature (ca. 300 to 450° C.) and under high pressure of hydrogen (ca., about 90 to 120 atm). The energy and infrastructure required to maintain such reaction conditions contributes significantly to refining costs for petroleum-based fuels and chemicals. Hence, there is a demand for inexpensive, low energy, and environmentally benign catalytic processes for industrial-scale production of fuels and commodity chemicals.

Accordingly, it would be useful to design catalysts that are both inexpensive and possess properties that are suitable for catalytic processes such as hydrodesulfurization.

SUMMARY

Generally, there is provided a transition metal catalyst of general Formula I:

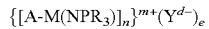  Formula I where:

A is a monoanionic σ-bonded ligand (e.g., hydrocarbyl, thiolate, alkoxide) that will undergo hydrogenolysis in the presence of hydrogen or hydrosilane;

M is a Fe, Co, or Ni;

n equals 2 to 4;

m equals 0, 1, 2, 3, 4 (up to a maximum of n);

Y is a weakly-coordinating or non-coordinating counter-ion, of formal negative charge 'd', and with stoichiometry 'e' such that d·e=m, and the charge of the counter-ion(s) offsets that of the cluster;

$R_3PN$ is an anionic phosphoranimide ligand of structure:

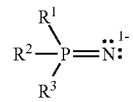

where:

$R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and/or Group 16 element, and silicon; $R^1$, $R^2$, $R^3$ may also be linked to give cyclic systems, using linkages such as aliphatic cyclic systems; and wherein the M to $R_3PN^-$ ratio in the catalyst is 1:1.

The oxidation state of the M in Formula I is +2 or +3, depending of the value of m.

Complexes of general Formula I that differ only in the value of 'm' represent a subclass of catalysts with the same cluster composition but different electronic states. The neutral "parent" clusters (when m=0), are described by Formula II below. The compounds of Formula II are the synthetic precursors to the electronically modulated cluster analogs of Formula I (when m≠0).

  Formula II wherein A, M, n, and $NPR_3$ are as defined for Formula I above.

According to one aspect of the invention, there is provided a method of synthesis of transition metal catalysts of Formula I as defined above, the method involving treatment of the parent cluster of Formula II as defined above with an outer-sphere oxidant. For example, the outer-sphere oxidant may be an inorganic or organic oxidant. Inorganic oxidants may include, but are not limited to: cations (e.g. ferrocenium, silver (I), copper(II), Fe(III), or Ce (IV) salts), anionic complexes (e.g. $[IrCl_6]_2^-$, $[PtCl_6]_2^-$), neutral compounds (e.g. $[Ni(tfd)_2]$ and $[Mo(tfd)_3]$), and main group oxidants (e.g. halogens, nitrosonium salts). Organic oxidants may include, but are not limited to: radical cations (e.g. $[N(aryl)_3]^+$, thianthrenes), carbocations (trityl or tropylium salts), and quinone derivatives.

Complexes of Formula II can be prepared from compounds of Formula III as shown below, by treatment of the compounds of Formula III with a nucleophilic reagent:

  Formula III where:

m=2 to 4;

M is Fe, Co, or Ni;

n=2 to 4;

X can be any halide or pseudohalide; and $R_3PN$ is as defined for the compound of Formula I above.

According to another aspect, there is provided a method of synthesis of a transition metal catalyst of Formula II comprising treating a precursor complex of Formula III ($[(MNPR_3)_nX_m]$) with a nucleophilic reagent functionally comprising the anion of A, in an amount sufficient to displace the remaining halide(s) under the conditions of the reaction. In one embodiment, the nucleophilic reagent is an alkylating agent such as an alkyl, an alkenyl, an aryl, or a heteroatom (such as oxygen or sulfur).

According to another aspect, there is provided a generalized method of synthesis of a complex of Formula III from an anionic metathesis reaction between a metal salt selected from the group consisting of $MX_m$ and $L_aMX_m$ and an alkali or alkaline metal salt of a phosphoranimide ligand. This reaction is illustrated below:

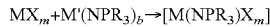

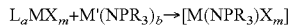

wherein:

m on the metal salt $MX_m$ and $L_aMX_m$ is 2 to 3;

a=1 to 4;

M is Co, Ni or Fe;

X is a halide or pseudohalide;

M' is an alkali or alkaline metal (for example, the alkali metal salts could be lithium, sodium, potassium, and cesium; and the alkaline earth metal could be magnesium);

$NPR_3$ is as defined above for the compound of Formula I; and

L can be a weak two-electron dative donor molecule selected from the group consisting of monodentate, bidentate dialkyl ethers and thioethers. For example, L may be tetrahydrofuran, 1,2-dimethoxyethane, dioxane, dimethylsulfide; or selected from a group of stronger, but dissociable donor molecules. As one skilled in the art would appreciate, L can be widely varied. Examples of L include: monodentate or bidentate tertiary amines (e.g., tetramethylethylenediamine), non-acidic nitriles (e.g. PhCN), isonitriles (e.g., tert-butylisonitrile), triarylphosphines (e.g., tri-(o-tolyl)phosphine).

According to another aspect, there is provided a method of synthesis of a parent transition metal catalyst of Formula II involving treating a metal salt selected from the group consisting of $MX_m$ and $L_aMX_m$ first with a nucleophilic reagent functionally comprising an anion A, followed by addition of an anionic phosphoranimide ($R_3PN^-$) without isolation of any intermediates. In this aspect, A, M, X, $R_3PN^-$ are as described in Formula I above, and m on $MX_m$ and $L_aMX_m$=2 to 3 and a=1 to 4.

In one embodiment, there is provided a method of synthesis of the mixed-valent cluster $[MeCo(NPEt_3)]_4PF_6$ comprising reacting the parent cluster of formula $[MeCo(NPEt_3)]_4$ with the one electron oxidant $Cp_2FePF_6$.

In another embodiment, there is provided a method of synthesis of the parent complex $[MeCo(NPEt_3)]_4$ comprising reacting a compound of formula $[Co(NPEt_3)Cl]_4$ with $Me_2Mg \cdot dioxane$ using dioxane as solvent.

In another embodiment, there is provided a method of synthesis of the precursor $[BrFe(NP^tBu_3)]_2$ comprising reacting $FeBr_2$ with $LiNP^tBu_3$.

In another embodiment, there is provided a method of synthesis of $[CoCl(NPEt_3)]_4$, comprising reacting $CoCl_2$ with $LiNP^tBu_3$.

In another embodiment, there is provided a method of synthesis of $[MeFe(NP^tBu_3)]_2$ comprising reacting $FeCl_2$ with MeLi at low temperature followed by $LiNP^tBu_3$.

DETAILED DESCRIPTION

Figure 1:
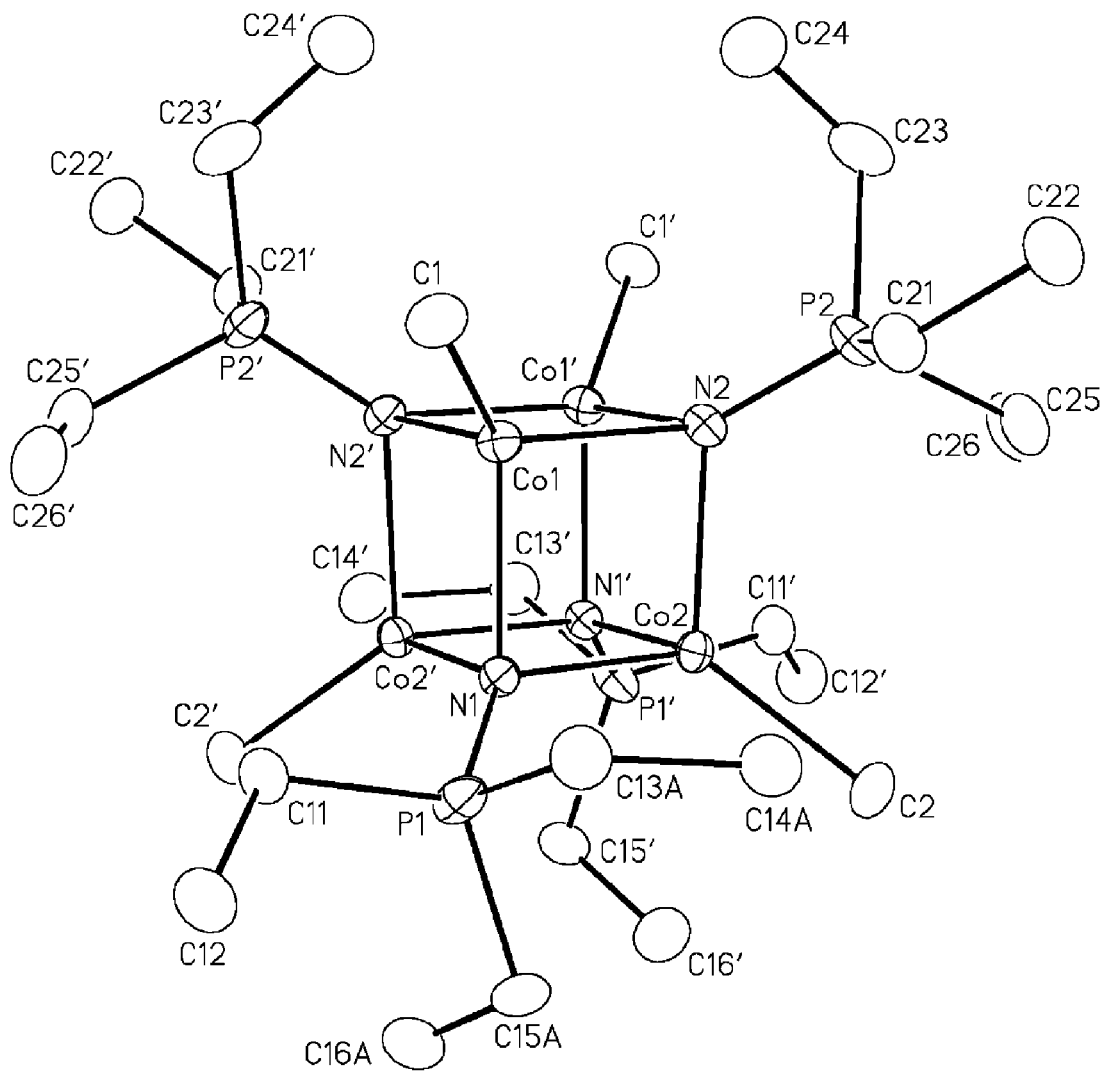
FIG. 1 shows an ORTEP diagram depicting the X-ray crystal structure of $[MeCo(NPEt_3)]_4$.

First row transition metal catalysts are generally believed to possess intrinsically low activity. Catalytic activity can be enhanced by assembling multiple metal centres into discrete ligand-supported clusters. In this arrangement, neighbouring metals can act as sinks or reservoirs of electron density, or react synergistically with reagents and/or substrates, facilitating processes that typically lie beyond the scope of a single metal. Moreover, the electronic characteristics of ligand-supported clusters can be manipulated to modify the degree to which the metals can interact, which in turn modulates the reactivity of the cluster. In this way, the activation process and catalytic activity of ligand-supported metal clusters can be optimized as a function of the specific oxidation state(s) of the catalytic entity.

Assembling first-row transition metals into discrete ligand-supported clusters can induce reactivity uncharacteristic of monomeric first-row transition metal catalysts. Metals in a cluster can interact directly (via bonding) or indirectly (through the ligand-bonding framework that connects them). Ligand frameworks can be selected strategically to facilitate both such interactions by supporting the metal centers at suitable distances from each other, with connections that efficiently link electronic environments. Modulating the electronic state of a cluster, by adding or removing electrons, can alter the bonding arrangement in a cluster, which affects the degree to which the metals interact and, accordingly, alters the reactivity. When metal-metal interactions are present within a cluster, the effects of removing or adding an electron from one metal can be distributed among all the participating metals. As a result, fractional changes to the oxidation states of metal ensembles can induce profound changes in cluster reactivity. Such subtle electronic modifications can provide a means to energize and optimize the catalytic activity of a small metal cluster.

In the case of discrete ligand-supported clusters and reductive catalysis, both catalyst activation and subsequent catalytic activity are affected by modifications to the cluster oxidation state. This feature provides a means to optimize cluster catalysts to activate and function under mild reaction conditions, while maintaining the desirable passivity of the pre-catalyst characteristics under storage conditions.

The factors that promote metal-ligand bond hydrogenolysis are fundamentally the same whether the step involves the activation of a pre-catalyst or the hydrogenolytic event in a catalytic cycle (e.g., sulphur removal during catalytic hydrodesulfurization). Thus, modulating a pre-catalyst for optimal activation also optimizes the reductive steps in a complex catalytic process.

Ideal pre-catalysts are thermodynamically stable and inactive under storage conditions for extended periods, but can be activated conveniently for catalysis. Pre-catalyst complexes for reductive chemical processes can include ancillary groups that react upon exposure to a terminal reductant (molecular hydrogen, hydrosilane), resulting in hydrogenolysis of the ancillary group-bond scission by molecular hydrogen or hydrosilane. In this way the pre-catalyst is transformed into an active form by facile installation of a reactive hydride bound to the metal. Ideally, ancillary groups can be strategically selected to ensure hydrogenolysis is facile and irreversible. The metal-bound atom of the ancillary group can be carbon, sulphur or oxygen.

To avoid the storage, handling, and manipulation of highly-sensitive reactive manifestations of the catalyst, the use of more stable pre-catalyst complexes is typically adopted. Under the reaction conditions, precatalysts can be activated from their passivated form. For reductive processes, precatalyst activation often involves the reaction of metal-bound ancillary groups with a terminal reductant (molecular hydrogen or hydrosilane) by hydrogenolysis. The ancillary group is released as a stable "protonated" molecule and a reactive "hydride" group is installed on the metal.

Many such ancillary groups will undergo hydrogenolysis with varying degrees of facility. The ancillary group is most often a hydrocarbyl fragment that undergoes irreversible activation by hydrogenolysis, yielding an inert hydrocarbon by-product. Other passivating groups (e.g. oxygen- or sulfur-based organic compounds, such as thiolates, alkoxides, and sulfido, oxo) can be used, as long as the group undergoes hydrogenolysis and removal from the reaction medium under acceptable conditions. Hydrogenolysis of metal-bound sulfur and oxygen compounds is also responsible for the extrusion of sulfur and oxygen from organic frameworks during catalytic hydrodesulfurization and hydrogenation.

Whether during precatalyst activation or as a step in the active catalytic cycle, the severity of the reaction conditions necessary to induce metal-ligand bond hydrogenolysis can be a function of multiple influences on the electronic environment at the metal center. As one skilled in the art would appreciate, judicious selection of coordinating ligands, based on their capacity to donate/accept electron density, has been established as a method for modulating catalytic activity in general and hydrogenolysis reactivity specifically. As one skilled in the art would also appreciate, it is less obvious that manipulating the oxidation state(s) of one or more of the metals in a polymetallic cluster can lead to the optimization of hydrogenolysis reactivity and can lead to rational catalyst design.

Electronically unsaturated, high-activity catalysts comprised of ligand-supported clusters of the later first row transition metal (e.g. cobalt, nickel, iron, copper, manganese, etc.) are disclosed. The metals in the clusters are each capped by auxiliary ligands that readily undergo hydrogenolysis to form active catalysts that are capable of energy-intensive reductive processes under mild conditions. The homovalent precatalyst complexes are electronically saturated but otherwise identical precatalyst clusters. While these precatalysts (e.g. compounds of Formula II) do activate and function in the same way as the electronically unsaturated clusters (e.g. compounds of Formula I), these clusters require harsher precatalyst activation conditions, suffer significant induction periods, and are not as catalytically efficient as the electronically modulated, oxidized clusters of the electronically unsaturated, high-activity catalysts.

The basis for the catalysts disclosed herein consists of a series of simple phosphoranimido metal halide clusters originally published by the Dehnicke and coworkers (see, for example, Dehnicke et al., (1998), *Phosphoraneiminato Complexes of Transition Metals*, Coordination Chemistry Reviews, 182 (1999) 19-65). While the basic heterocubane structural motifs of Dehnicke show a polymetallic metal scaffold, as outlined above, there are additional criteria necessary for reductive catalysis. The catalysts of the present disclosure adopt a different topology, dimensionality, and oxidation state from previously disclosed phosphoranimido metal clusters. In previous precatalyst clusters, the metals within each cluster are not differentiated in oxidation state (i.e. not mixed-valent), the system is not activated by hydrogenolysis, and the metals are in a lower initial oxidation state (+1) than the catalysts of the present disclosure.

In the present disclosure, the efficient, high yield replacement of terminal halide substituents with labile alkyl and other defined groups is important to enabling the precatalyst embodiments. The alkyl substituents undergo irreversible hydrogenolysis, efficiently installing highly reactive hydride groups on the now-active catalyst.

DEFINITIONS

As used throughout this disclosure, the term "alkyl" includes $C_1$ to $C_{18}$ straight chain, branched or cyclic alkyl groups such as, but not limited to, ethyl, propyl, isopropyl and t-butyl.

The term "aryl" includes aromatic hydrocarbons as substituents. Aryl groups may have one or more aromatic rings, which may be fused or connected by a connecting group or a bond. Aryl groups may also include one or more alkyl, aryl, or inert heteroatom-containing (N, O, Si) functionality as substituents located on the aryl group. Specific though non-limiting examples include, phenyl, tolyl, naphthenyl, biphenyl, alkoxy, N,N-dialkylamido.

The term "heteroaryl" includes aromatic ring systems that contain at least one heteroatom in at least one ring. Similar to the aryl groups, heteroaryl groups may have one or more aromatic rings, may be substituted or unsubstituted, and may be fused or appended to another ring, directly or through another group or bond.

The term "inert functional group" designates heteroatom-bearing hydrocarbyl fragments attached via the heteroatom to aryl and heteroaryl ligand substituents, as defined above, or appended to the terminus of a ligand substituent. The former serve to modulate, electronically and/or sterically, the chemical nature of the phosphoranimide ligand(s), changing but not impeding catalyst performance. The latter can function as a point of further chemical attachment(s) (i.e., derivatization), for example, in order to construct supported heterogeneous catalysts comprising chemically bonded or linked phosphoranimido-metal catalyst subunits grafted onto conventional or unconventional catalyst supports.

The term "heteroatom" refers to a Group 14 element other than carbon, or to a Group 15 or 16 element, preferably Si, N or O.

The term "pseudohalide" refers to anions with similar properties to halides, preferably $OSO_2R^-$, where R=Me, Ph, p-Tol, $CF_3$.

The term "weakly-coordinating counter-ion" refers to an outer-sphere (non-coordinating or nearly so) negatively charged species present to balance the charge on the partially oxidized, electronically unsaturated metal-phosphoranimido clusters. A person skilled in the art would appreciate the types of negatively charged species that could achieve this result in any particular case. Examples include, but are not limited to, triflate $(OSO_2CF_3)^-$, $PF_6^-$, $BF_4^-$, $BPh4^-$ and $B(C_6F_5)_4^-$.

Abbreviations: Me=methyl; Et=ethyl; Ph=phenol, Fe=iron, Ni=nickel, Co=cobalt; Si=silicon, O=oxygen, N=nitrogen and all other elements are designated by their symbol in the periodic table.

Catalysts

The present disclosure provides a class of transition metal catalysts of general Formula I:

{[A-M(NPR$_3$)]$_n$}$^{m+}$(Y$^{d-}$)$_e$     Formula I where:

A is a monoanionic ligand that will undergo hydrogenolysis in the presence of hydrogen or hydrosilane. Examples include alkyl (C1-18, primary, secondary), cycloalkyl (C3-C8), alkynyl, vinyl, aryl/heteroaryl, substituted aryl/heteroaryl or a functional group containing a heteroatom bound to the metal and selected from the group consisting of a Group 15 and/or Group 16 elements, preferably alkoxide or thiolate. A can also represent one half of a dianionic heteroatom such as sulfur (as sulfido) and oxygen (as oxo). In one embodiment, A is a small alkyl group that will undergo irreversible hydrogenolysis, thereby efficiently installing a reactive hydride group on the metal;

M is a late first row transition metal;
n equals 2 to 4;
m equals 0, 1, 2, 3, 4 up to a maximum of n;
Y is a weakly-coordinating or non-coordinating counter-ion, of formal negative charge 'd', and with stoichiometry 'e' such that d·e=m, and the charge of the counter-ion(s) offsets that of the cluster;

R$_3$PN is an anionic phosphoranimide ligand of general structure:

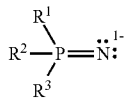

where:

R$^1$, R$^2$, R$^3$ can be the same group or different groups; R$^1$, R$^2$, R$^3$=alkyl (C$_{1-18}$, primary, secondary and tertiary alkyl), cycloalkyl (C3-C8), aryl/heteroaryl, substituted aryl/heteroaryl or an inert functional group containing at least one heteroatom selected from the group consisting of a heavy Group 14 element, or a Group 15 or Group 16 element, preferably O, N, Si; R$^1$, R$^2$, R$^3$ may also be linked to give cyclic systems, using linkages such as aliphatic cyclic systems; and wherein the M to R$_3$PN$^-$ ratio in the catalyst is 1:1.

In one embodiment, M is Fe, Co or Ni. The formal oxidation state of M is +2 or +3, depending on the value of m in the general formula.

Complexes of General Formula I that differ only in the value of 'm' represent a subclass of catalysts with the same cluster composition but different electronic states. The neutral "parent" clusters (where m=0 in Formula I), are described by Formula II and are the synthetic precursors to the electronically modulated cluster analogs of Formula I (where m≠0).

[A-M(NPR$_3$)]$_n$     Formula II wherein A, M, n, and NPR$_3$ are the same as described for Formula I.

In Formulae I and II, the value for n can vary with the steric and electronic nature of the anionic phosphoranimide ligand, R$_3$PN$^-$. For example, the catalysts may have integer values of n between 2 and 4, inclusive. In the embodiments wherein the phosphoranimide ligand contains bulky alkyl substituents R$^1$, R$^2$, and R$^3$, n is generally equal to 2. In other embodiments, wherein the phosphoranimide ligand contains less bulky substituents, n is generally equal to 4. In all embodiments, the transition metal may be Fe, Co, or Ni. In the Examples, Fe and Co are suitable metal centers for the catalysts. The chemical compositions of the catalysts described in this disclosure are uniformly consistent with a substance where the ratio of M to R$_3$PN$^-$ to A$^-$ is 1:1:1.

Complexes of Formula II can be prepared by treating a precursor complex of Formula III, as described below. The compound of Formula III has the following structure:

[(MNPR$_3$)$_n$X$_m$]     Formula III where:
m=2 to 4;
n=2 to 4;
M is Fe, Co, or Ni;
X can be any halide or pseudohalide;
R$_3$PN is an anionic phosphoranimide ligand of structure:

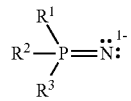

where
R$^1$, R$^2$, R$^3$ are the same group or different groups; R$^1$, R$^2$, R$^3$=alkyl (C$_{1-18}$, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic.

According to one aspect of the invention, there is provided a method of synthesis of a parent transition metal catalyst of Formula II comprising treating a compound of Formula III [(MNPR$_3$)$_n$X$_m$] with a nucleophilic reagent functionally comprising the anion of A, in an amount sufficient to displace some or, preferably, all of the halide(s). This reaction is illustrated below:

[(MNPR$_3$)$_n$X$_m$]+AM'→[A-M(NPR$_3$)]$_n$

The source of A, is a nucleophilic reagent, AM', where M' is alkali or alkaline earth metal, or a Group 13 reagent, such as but not limited to Li, Mg, K, Al, or B. The use of dioxane as the medium and a magnesium anion for this transmetallation reaction is a suitable embodiment and a factor in forcing complete exchange of the halide with AM' in complexes of Formula III. The methylation equilibrium should be driven to completion via the use of a solvent or additive to 'sequester' the magnesium salts and drive the reaction to completion. The sequestration may take place in solution or by phase separation (e.g. precipitation) of the magnesium halide salts formed during the reaction. While dioxane is suitable in this regard, other solvents that serve the same function (e.g. to drive the reaction to equilibrium) could be used and other alkali or earth metals may be used. That said, in some solvent systems and with some M' counter-ions, such exchange reactions do not generally lead to pure, tractable products wherein the halides groups have been completely replaced. A person skilled in the art could select suitable solvents based on the teachings in the present disclosure.

The formation of an insoluble dioxane-chelated magnesium salt drives the equilibrium to completion. This strategy allows for the preparation of hydrocarbyl-capped late metal phosphoranimide clusters. The alkyl substituents of Formula I undergo irreversible hydrogenolysis, installing highly reactive hydride groups on the now-active catalyst. The halide precursors of Formula III are generally not suitable precatalysts for reductive chemistry: the efficient, high yield replacement of terminal halide substituents with labile alkyl and other defined groups is important to enabling the precatalyst embodiments.

An example of a nucleophilic reagent that may be used in the above-mentioned process is an alkylating agent. More specifically, the catalysts of Formula II can be produced by reacting the compounds of Formula III with an alkylating agent functionally comprising the anion of A. The alkylating agent may be, for example, a hydrocarbyl anion (such as methyl, ethyl, vinyl, alkynl, an aryl, etc.), an oxygen anion or a sulfur anion.

According to another aspect, there is provided a method of synthesis of a series of catalysts of Formula I. The method involves treatment of a neutral parent cluster (Formula II) with outer-sphere oxidants. The resulting catalysts have the same cluster composition as Formula II compounds but different electronic states, (e.g. the resulting products can be described by Formula I).

The outer sphere oxidant may be any compound that has sufficiently strong oxidation potential to extract one or more electrons from the precatalyst. The weakest outer sphere oxidant would remove only one electron from the catalyst cluster, whereas stronger oxidants could remove solely one electron or could remove more than one electron. However, the number of electrons removed does not depend solely on the oxidation potential of the metal, but also, on the ratio of the oxidant to the cluster. Thus, the oxidant could be chosen to yield anywhere from a positive charge of 1 to 4 on the cluster.

As one skilled in the art will appreciate, many outer-sphere oxidants have redox potentials suitable for the required oxidations. Most commonly, outer-sphere oxidants are categorized as inorganic or organic oxidants. Inorganic oxidants include, but are not limited to: cations (e.g. ferrocenium, silver (I), copper(II), Fe(III), or Ce (IV) salts), anionic complexes (e.g. $[IrCl_6]_2^-$, $[PtCl_6]_2^-$), neutral compounds (e.g. $[Ni(tfd)_2]$ and $[Mo(tfd)_3]$), and main group oxidants (e.g. halogens, nitrosonium salts). Organic oxidants include, but are not limited to: radical cations (e.g. $[N(aryl)_3]^+$, thianthrenes), carbocations (trityl or tropylium salts), and quinone derivatives.

As mentioned above, electronic-state modulation across a series of clusters manifests in subtle changes in cluster geometries. Such structural changes affect the metal-metal interactions (either via direct M-M bonding, or through the nitrogen linkages), and therefore the propensity for a cluster to mediate hydrogenolytic processes. Partial oxidation also provides a new, low-lying empty molecular orbital, suitable for facile binding and processing of the reductant. Such an orbital can be absent or impractically high in energy in the non-oxidized cluster, as is the case in both cobalt and nickel precatalysts of the present disclosure. These factors affect the rate of precatalyst activation, as well as the rate of turnover in the catalytic cycle. Taken together, cluster electronic-states can be tailored for effective catalysis.

A convenient, reliable, and broad applicable method of synthesis for the precursors of Formula III is required to ensure scalability of the technology disclosed herein. It is known that halide clusters of Formula III may be prepared by a solvent-free procedure using a high temperature "molten state" process that relies upon liquefication of the trialkylsilylphosphoranimide precursor ($Me_3SiNPR_3$, R=Me or Et) to serve as the reaction medium. However, this procedure is not adaptable to any silylphosphoranimide that does not melt at an accessible temperature, severely limiting the scope of the process.

In the present disclosure, phosphoranimidometal halide clusters of Formula III are prepared via salt metathesis at low temperature, exchanging one anion for another in the coordination sphere of the metal. This disclosure provides a new and general methodology for the synthesis of the compounds of Formula III, by treatment of a transition metal salt of formula $MX_m$ or $L_aMX_m$ with a stoichiometrically appropriate alkali or alkaline metal salt of a phosphoranimide ligand. This method of synthesis is carried out under an inert atmosphere and relatively low temperature.

According to another aspect, there is provided a generalized method of synthesis of a complex of Formula III from an anionic metathesis reaction between a metal salt selected from the group consisting of $MX_m$ and $L_aMX_m$ and an alkali or alkaline metal salt of a phosphoranimide ligand. This reaction is illustrated below:

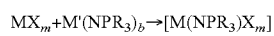

$MX_m + M'(NPR_3)_b \rightarrow [M(NPR_3)X_m]$

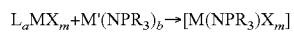

$L_aMX_m + M'(NPR_3)_b \rightarrow [M(NPR_3)X_m]$ wherein:
m on $MX_m$ and $L_aMX_m$=2 to 3;
a=1 to 4;
M is Co, Ni or Fe;
X is a halide or pseudohalide;
M' is an alkali or alkaline metal (for example, the alkali metal salts could be lithium, sodium, potassium, and cesium; and the alkaline earth metal could be magnesium);
$NPR_3$ is as defined above for the compound of Formula I; and
L can be a weak two-electron dative donor molecule selected from the group consisting of monodentate, bidentate dialkyl ethers and thioethers. For example, L may be tetrahydrofuran, 1,2-dimethoxyethane, dioxane, dimethylsulfide; or selected from a group of stronger, but dissociable donor molecules. As one skilled in the art would appreciate, L can be widely varied. Examples of L include: monodentate or bidentate tertiary amines (e.g., tetramethylethylenediamine), non-acidic nitriles (e.g. PhCN), isonitriles (e.g., tert-butylisonitrile), triarylphosphines (e.g., tri-(o-tolyl)phosphine).

In the Examples of the present disclosure, Fe, and Co are shown to be suitable as the metal centers. In some embodiments, X can be, but is not limited to, $F^-$, $Cl^-$, $Br^-$, $I^-$, or $OSO_2R^-$, where [inter alia] R=Me, Ph, p-Tol, $CF_3$.

According to another aspect, there is provided a method of synthesis of a transition metal catalyst of Formula II involving treating a metal salt selected from the group consisting of $MX_m$ and $L_aMX_m$ first with a nucleophilic reagent functionally comprising an anion A, followed by an anionic phosphoranimide ($NPR_3$) without isolation of any intermediates; wherein: Groups A, M, X, ($NPR_3$) are as defined above for Formula I and m, and a are as defined for Formula III above. This aspect is important for the preparation of alkyl-capped phosphoranimide clusters wherein the phosphoranimide based R groups are sterically encumbering. Larger R groups force lower cluster dimensionality, which fundamentally effects reactivity. Complexes with large R groups tend to conproportionate under the preparatory conditions described in this aspect, leading to unstable dialkyl metal complexes and bis(phosphoranimide) clusters.

In one embodiment, the structurally characterized catalysts are a family of tetrameric clusters that differ only in the charge associated with the heterocubane core, which consequently differ also in the number of charge-balancing counter-ions, following the general Formula IV:

$$\{[A\text{-}M(NPR_3)]_4\}^{m+}(Y^{d-})_e \qquad \text{Formula IV}$$

wherein A, M, Y, and NPR$_3$ and m are as defined above in the compound of Formula I.

The catalysts of Formula IV (as well as those of general formulae I and II) embody two non-design elements: [1] Discrete homoleptic ligand-supported cluster catalysts wherein the catalyst performance can be readily manipulated by modulation of the initial oxidation state of the cluster. [2] Strategic inclusion of ligand "triggers" (i.e., A) that will readily undergo hydrogenolysis in the presence of a reductant, transforming the cluster from an inactive form (i.e., passivated, to a greater or lesser extent) to the active hydridic catalyst.

In one embodiment, the catalysts of Formula IV are discrete tetrametallic transition metal clusters having the following graphical structure:

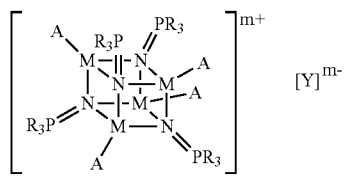

wherein
the ratio of M to NPR$_3$ is 1:1;
m=0-4;
A, M, X and NPR$_3$ are as defined in the compound of Formula I.

In one embodiment, m=1.

Comparison of the X-ray structures of catalysts of Formula IV (X-ray structures of M=Co, R=Et, A=Me, m=0 or 1, are provided below) reveals the link between the oxidation state of the metals in the cluster, and the cluster bonding and geometry. The lengths of the linking C—N bonds are significantly shorter after oxidation [1.994(4) Å in the cationic cobalt cluster vs. 2.034(4) Å in the neutral cobalt cluster]. The distance between cobalt atoms is further affected by changes in Co—N—Co bond angles (Co—Co bond length=2.7181(9) Å in the cationic cluster, and 2.8727(6) Å in the neutral cluster). This change in metal proximity is related to the enhancement in metal-metal electronic interactions which are manifest in disparate magnetic characteristics ($\mu_b$=4.90 vs. 5.82, for the neutral and singly cationic cobalt clusters, respectively). The electronic state of the singly cationic cobalt cluster is preferred for activation under mild conditions, and for reductive catalysis as detailed below.

The characterized catalysts of Formula IV (m=0, 1) differ from those of Dehnicke, et al. ((1998), *Phosphoraniminato Complexes of Transition Metals*, Coordination Chemistry Reviews, 182 (1999) 19-65]). Generally, Dehnicke does not teach changing the oxidation state of phosphoranimido metal halide clusters as a method for tuning reactivity, stability, or function. Outer-sphere one-electron oxidation of the neutral clusters of Formula IV to the corresponding mixed-valent M(II)/M(III) precatalysts activates the catalysts electronically by providing a vacant molecular orbital on the metal for binding of the reductant necessary for the hydrogenolysis of the M-A bond(s). The cationic catalyst mediates hydrogenolysis under much milder conditions than possible in the absence of the mixed-valent oxidation state, in which all of the d-orbitals are occupied by at least one electron. Simultaneously, oxidation also modestly passivates the precatalyst toward reaction with and decomposition induced by air or environmental moisture.

Inner-sphere oxidation of the cluster by elemental sulfur or controlled treatment with oxygen-transfer reagents also results in oxidative passivation. As inferred by the facile hydrogenolysis of sulfur- and oxygen-containing precatalysts of Formula I (A=thiolate or alkoxy), the presence of dianionic sulfido- or oxo-ligands on the catalyst surface does not interfere with reductive activation of the catalysts, undergoing M-S and M-O hydrogenolysis under pretreatment with molecular hydrogen. At the same time, the sulfide- or oxided-precatalysts become both air- and moisture-stable, requiring no special storage or transfer precautions. Transition metal sulfides and oxides are industrially useful precatalysts for hydrogenation and hydrodesulfurization of petroleum feedstocks.

The complexes of Formulae I-IV have metal centers supported by bridging phosphoranimide ligands, triply bridging for clusters of relatively small phosphoranimide ligands and doubly-bridging for sterically large ligands. Compared to the corresponding trialkylphosphine ligands, for example, the phosphoranimide (P=N) functional group displaces the three R groups further away from the metal centers, allowing substrates greater steric access to the metal centers than present in typical cluster complexes. The phosphoranimide nitrogen center can donate up to a total of three electron pairs to the metal(s), which leads to bridging coordination at the nitrogen and short metal-metal distances. This bonding arrangement imposes a significant degree of electronic interactions among the metals, either directly (i.e., bonding), or indirectly through the linking nitrogen atoms. In conjunction with the absence of ancillary ligands and/or exogenous donor molecules, phosphoranimide bridging allows for the stabilization of coordinatively unsaturated metal centers in the catalysts of this disclosure.

As a person skilled in the art would appreciate, complexes of Formula I can adopt various modes of aggregation. As a result, compounds of Formula I represent a library of functionally related catalysts. Structurally characterized compounds of Formula IV comprise a subclass of catalysts with compositions represented by Formula I. Compounds of Formula IV result from the selection of a phosphoranimide ligand with substituents small enough to allow for triply-bridging coordination. Catalysts supported by phosphoranimide ligands of electronic and steric properties similar to, for example, triethyl phosphoranimide, may adopt such tetrameric structures. However, unless specifically provided in the Examples, the catalysts of the present disclosure do not represent specifically characterized structures.

The synthetic strategies disclosed herein provide methods for the synthesis of other hydrocarbyl-capped electronically tuned base metal catalysts supported by bridging imido-like anionic ligands wherein the M:L:A ratio is maintained at 1:1:1. These imido-stabilized catalysts, include trialkylphosphoranimides, but can be extended to other monoanionic ligands of similar bonding character.

The non-limiting examples below serve to illustrate the embodiments described above.

EXAMPLES

Example 1

[MeCo(NPEt$_3$)]$_4$ and Method of Synthesis

A methyl-capped cobalt phosphoranimide catalyst (shown in FIG. 1 and referred to herein as the neutral cobalt catalyst) having the formula shown below is synthesized as an example:

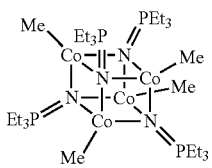

To prepare this catalyst, 0.55 mmol of [CoCl(NPEt$_3$)]$_4$ and 0.22 mmol of Me$_2$Mg.dioxane are separately dissolved in 8 mL portions of dioxane in 15 mL screw-capped vials under an inert atmosphere, for example, in a nitrogen or argon-filled drybox. Both solutions are cooled to 12° C. The Me$_2$Mg.dioxane solution is added drop-wise to the [CoCl(NPEt$_3$)]$_4$ with occasional stirring over a two hour period with the temperature constant at 12° C. The solvent is removed in vacuo and the residue is triturated with 4 mL portions of cold pentane thrice. The pentane washes are pooled and filtered through celite. The solvent is removed in vacuo, giving a green powder in 86% isolated yield. The product crystallizes as dark green prismatic crystals from liquid-liquid layering, slowly diffusing hexane into a concentrated solution of the crude product at −35° C.

The product is characterized by X-ray crystallography, magnetic susceptibility measurement by the Evan's method (Evans, D. F. J. J. Chem. Soc. 1959, 2003-2005, which is herein incorporated by reference), and elemental analysis (vide infra).

FIG. 1 shows an ORTEP (Oak Ridge Thermal Ellipsoid Plot Program) diagram depicting the X-ray crystal structure of [MeCo(NPEt$_3$)]$_4$. The calculated elemental composition of the neutral cobalt catalyst is C, 40.79%; H, 8.80%; N, 6.80%. The determined elemental composition is C, 40.69%; H, 8.80%; N, 6.68%. Solution magnetic susceptibility experiments revealed that the neutral cobalt catalyst is a 4.01-electron paramagnet ($\mu_{eff}$=4.90 $\mu_{Bo}$) at room temperature.

Example 2

[MeCo(NPEt$_3$)]$_4$PF$_6$ and Method of Synthesis

A cationic methyl-capped cobalt phosphoranimide catalyst (shown in FIG. 1 and referred to herein as the singly-cationic cobalt catalyst) having the formula shown below is synthesized as an example:

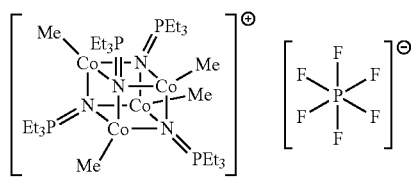

To prepare this catalyst, 0.31 mmol of [MeCo(NPEt$_3$)]$_4$ and 0.28 mmol of Cp$_2$FePF$_6$ are dissolved/suspended in 5 ml portions of toluene in 15 mL screw-capped vials under an inert atmosphere, for example, in a nitrogen- or argon-filled drybox. Both samples are cooled to −35° C. in a dry-box freezer for an hour. The Cp$_2$FePF$_6$ supsension is added drop-wise into the [MeCo(NPEt$_3$)]$_4$ solution over a four-hour period with the temperature constant at −35° C. After two hours of stirring at room temperature, the reaction solids were separated by filtration through a glass frit and washed with 15 mL portions of hexane thrice. The remaining solids are dissolved in 15 mL of tetrahydrofuran and filtered through a plug of Celite. The solvent is removed in vacuo, giving a 91% yield.

Figure 2:
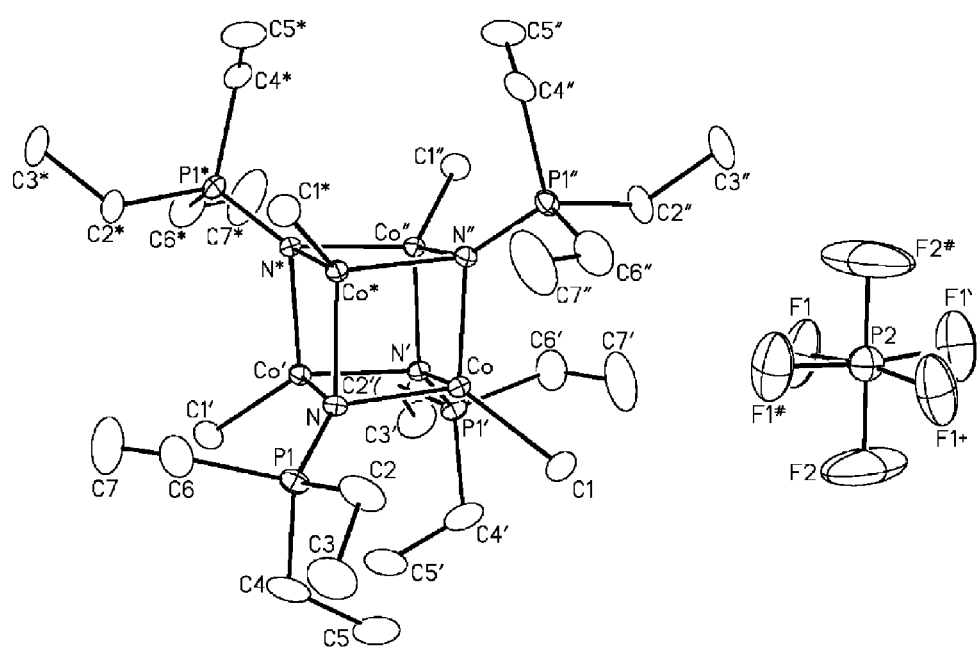
FIG. 2 shows an ORTEP diagram depicting the X-ray crystal structure of $[MeCo(NPEt_3)]_4P4_6$.

FIG. 2 shows an ORTEP (Oak Ridge Thermal Ellipsoid Plot Program) diagram depicting the X-ray crystal structure of [MeCo(NPEt$_3$)]$_4$PF$_6$. The calculated elemental composition of the singly-cationic cobalt catalyst is C, 34.69%; H, 7.49%; N, 5.78%. The determined elemental composition is C, 34.75%; H, 6.96%; N, 5.62%. Solution magnetic susceptibility experiments revealed that the neutral cobalt catalyst is a 4.90-electron paramagnet ($\mu_{eff}$=5.82 $\mu_{Bo}$) at room temperature.

Example 3

[MeFe(NP$^t$Bu$_3$)]$_2$ and Method of Synthesis

A methyl-capped iron phosphoranimide catalyst (referred to herein as the neutral iron catalyst) having the formula shown below is synthesized as an example:

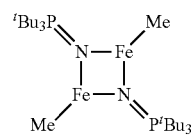

To prepare this catalyst, 8.5 mmol of FeCl$_2$ is suspended in 30 mL of tetrahydrofuran (THF) and cooled to −80° C. An ether solution of 9.1 mmol MeLi was added drop-wise over 30 minutes. The reaction is stirred for three hours at −80° C. A suspension of 8.7 mmol LiNP$^t$Bu$_3$ in 90 mL THF is cooled to −78° C. and added slowly via cannula to the reaction. The reaction is stirred for 16 hours at −80° C. and then warmed to room temperature. The THF is removed in vacuo and the residue suspended in 60 mL of pentane. The suspension is stirred for 24 hours, then filtered through a plug of Celite. The pentane is removed in vacuo and the residue dried under high vacuum for 16 hours. The residue is suspended in 40 mL of cold pentane, and filtered through a plug of Celite. The cold filtration is repeated and then the pentane removed in vacuo. The yield for this reaction is 29%. The product was characterized by elemental analysis.

The calculated elemental composition of MeFeNP$^t$Bu$_3$.0.3 THF is C, 55.22%; H, 10.57%; N, 4.54%. The determined elemental composition is C, 55.05%; H, 10.48%; N, 4.93%.

Example 3

In-Situ Preparation of {[MeFe(NP$^t$Bu$_3$)]$_2$}$^{m+}$ and Catalytic Activity A methyl-capped cationic iron phosphoranimide catalyst (referred to herein as the cationic iron catalyst) is synthesized in-situ and used for catalysis as an example. By "in situ", it is meant that the catalyst is not subject to isolation and purification after synthesis, but instead prepared and used directly in the catalytic process.

The preparation of reaction mixture is conducted under an inert atmosphere, for example, in a nitrogen-filled dry box. A Teflon-sealed reactor is charged with 131 mg (0.71 mmol) dibenzothiophene, 21 mg (3.6×10$^{-2}$ mmol) [FeMe(NP$^t$Bu$_3$)]$_2$, 6 mg (1.8×10$^{-2}$ mmol) Cp$_2$FePF$_6$, 56 mg (1.4 mmol) KH, 10 mL toluene, and a stir bar. The reactor was taken out of the dry box and connected to a hydrogen manifold. The reaction vessel is then charged with $H_2$ (1 atm), employing strict inert-atmosphere laboratory techniques. The reaction mixture is then stirred at a 1200 rpm for 4 hours in an oil bath at 130° C.

The reactor is cooled to room and the reaction mixture quenched with a 10% HCl solution. The organic products are extracted through diethyl ether-water extractions using three 6 mL portions of diethyl ether. The diethyl ether fractions are pooled, dried with anhydrous $Na_2SO_4$ and filtered through a small column of Florisil™. The diethyl ether is removed in vacuo and the weighed residue dissolved in $CDCl_3$ for $^1$H-NMR and GC-MS analyses. The process as described gives 22% conversion and produces biphenyl (8%) and 2-phenylthiophenol (14%), exclusively, as products.

Example 5

[Fe(NP$^t$Bu$_3$)Br]$_2$ and Method of Synthesis

A halide functionalized iron phosphoranimide precatalyst having the formulation below has been synthesized as an example.

To prepare this precatalyst, 4.3 mmol FeBr$_2$.(dme) and 4.4 mmol LiNPtBu$_3$ were each suspended in 100 mL of tetrahydrofuran (THF) in separate Schlenk flasks. Both suspensions were cooled to −78° C. using dry ice/acetone baths and then the LiNPtBu$_3$ suspension was slowly added to the FeBr$_2$.(dme) suspension via cannula. The reaction was slowly warmed to room temperature over the next 16 hours. The THF was removed in vacuo and the residue extracted into toluene, then filtered twice through celite. The toluene was removed in vacuo. The yield of this reaction was 41%. Crystals were grown from concentrated THF at −35° C. in a dry-box freezer and the compound was characterized by X-ray crystallography.

Figure 3:
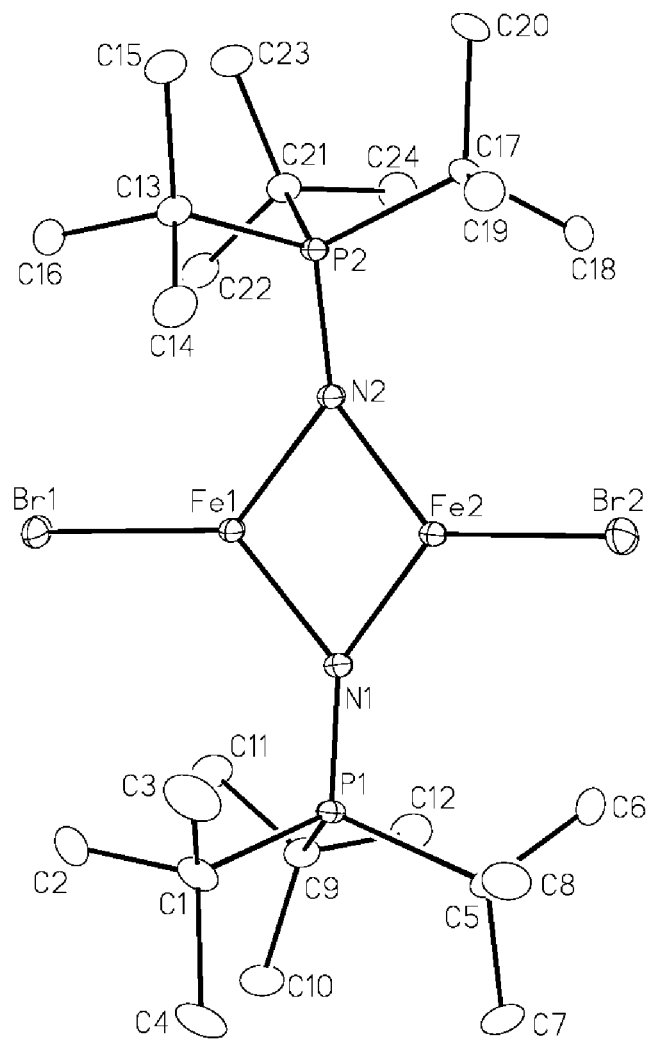
FIG. 3 shows an ORTEP diagram depicting the X-ray crystal structure of $[FeBr(NP^tBu_3)]_2$.

FIG. 3 shows an ORTEP diagram depicting the X-ray crystal structure of [Fe(NPtBu$_3$)Br]$_2$.

This pre-catalyst is presumed to be a dimer, and accordingly, the active compounds of Formula II that are derived from this pre-catalyst are also believed to be dimeric. As noted above, the catalysts of the present disclosure are not limited to any particular structure, but rather represent a library of catalysts.

Example 6

Electronically Tuned Catalysts: Differences Between Neutral and Cationic Cobalt Catalysts Experiments were carried out to establish the ability of the precatalysts of formula [MeCo(NPEt$_3$)]$_4$ and [MeCo(NPEt$_3$)]$_4$PF$_6$ to activate under mild conditions, and to mediate the catalytic hydrodesulfurization of dibenzothiophene. Under 500 psi of hydrogen, [MeCo(NPEt$_3$)]$_4$ does activates slowly and mediates the catalytic hydrodesulfurization of dibenzothiophene (eqn. 1).

The cationic cluster [MeCo(NPEt$_3$)]$_4$PF$_6$ does not require high pressure $H_2$ for activation. This precatalyst activates under one atmosphere $H_2$ at 150° C. without an induction period, and is a markedly more efficient catalyst (eqn. 2). The neutral cobalt cluster [MeCo(NPEt$_3$)]$_4$ can be converted into the cationic cluster [MeCo(NPEt$_3$)]$_4$PF$_6$ in situ via addition of Cp$_2$FePF$_6$, as described above.

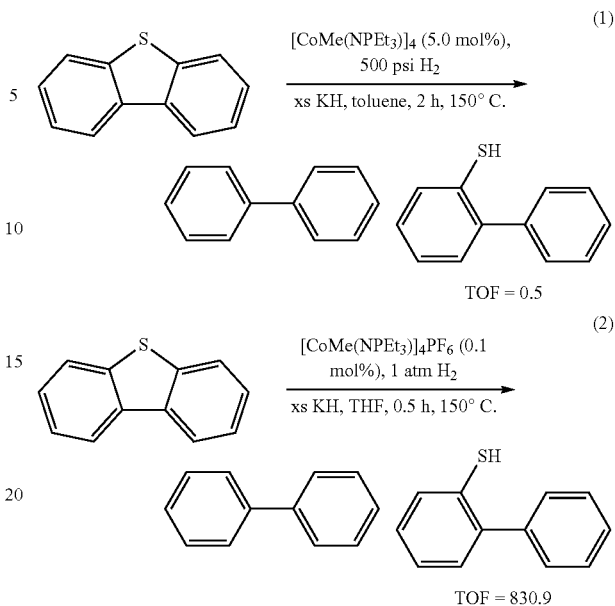

Turnover frequency ("TOF")=moles of substrate converted per mole of cluster per hour (each turnover requires two C—S bond cleavages); in cases wherein a mixture of the partially and fully-desulfurized products (thiol and hydrocarbon, respectively) was obtained, one catalytic turnover was similarly calculated as two moles of C—S bonds activated per mole of cluster per hour.

The invention claimed is:

1. A compound of Formula I, wherein Formula I has the structure:

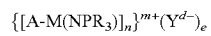   Formula I where:
  A is a monoanionic σ-bonded ligand that undergoes hydrogenolysis in the presence of hydrogen or hydrosilane;
  M is a late first row transition metal;
  n equals 2 to 4;
  m equals 0 to 4 up to a maximum value of n;
  Y is a weakly-coordinating or non-coordinating counter-ion, of formal negative charge 'd', and with stoichiometry 'e' such that d·e=m, and the charge of the counter-ion(s) offsets that of the cluster;
  R$_3$PN is an anionic phosphoranimide ligand of structure:

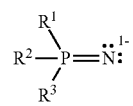

where:
  R$^1$, R$^2$, R$^3$ can be the same group or different groups; R$^1$, R$^2$, R$^3$=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and/or Group 16 element, and silicon; R$^1$, R$^2$, R$^3$ may also be linked to give cyclic systems, using linkages such as aliphatic cyclic systems; and
  wherein the M to R$^3$PN$^-$ ratio is 1:1.

2. The compound of claim 1, where n=4.
3. The compound of claim 1, wherein M is Fe, Co or Ni.
4. The compound of claim 1, wherein M is Fe.
5. The compound of claim 1, wherein M is Co.
6. The compound of claim 1, wherein M is Ni.
7. The compound of claim 1, wherein each of $R^1$, $R^2$ and $R^3$ are a C1 to C3 alkyl.
8. The compound of claim 1, wherein $NPR_3$=$NPEt_3$ or NPt-butyl.
9. The compound of claim 1, wherein A=methyl.
10. The compound of claim 1, wherein $(Yd^-)_e$ is $PF_6$.
11. The compound of claim 1 having formula: $[MeCo(NPEt_3)]_4$.
12. The compound of claim 1 having formula: $[MeCo(NPEt_3)]_4PF_6$.
13. The compound of claim 1 having formula: $[MeFe(NP^tBu_3)]_2$.
14. The compound of claim 1, wherein m=0 and thereby, there is no $(Yd^-)_e$.
15. The compound of claim 14, wherein A=Me, and M is Co or Ni.
16. The compound of claim 1, having the formula: $[MeNi(NPEt_3)]_4$.
17. A method for synthesizing a compound of Formula II:

$$[A-M(NPR_3)]_n$$

where:
A is a monoanionic σ-bonded ligand that undergoes hydrogenolysis in the presence of hydrogen or hydrosilane;
M is Co, Ni or Fe;
n equals 2 to 4;
$R_3PN$ is an anionic phosphoranimide ligand of structure:

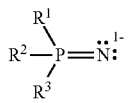

where: $R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and Group 16 element, and silicon; $R^1$, $R^2$, $R^3$ may also be linked to give cyclic systems; and wherein the M to R3PN⁻ ratio in the catalyst is 1:1,
the method comprising:
reacting a precursor of Formula III: $[(MNPR_3)_nX_m]$, where M, $NPR_3$, and X are as defined for the compound of Formula II and m=2 to 4, with a nucleophilic reagent AM' comprising the anion of A where M' is alkali or alkaline earth metal, or a Group 13 reagent.

18. The method of claim 17, wherein the amount of A is sufficient to displace some or all of the X.
19. The method of claim 17, wherein M is Co, Fe or Ni.
20. The method of claim 17, wherein M' is Mg.
21. The method of claim 17, wherein the method is carried out in dioxane.
22. The method of claim 17, wherein the nucleophilic reagent is an alkylating agent selected from the group consisting of a hydrocarbyl anion, an oxygen anion, and a sulfur anion.

23. A method of synthesis of the compound of Formula I having formula:

$$\{[A-M(NPR_3)]_n\}^{m+}(Y^{d-})_e \qquad \text{Formula I}$$

where:
A is a monoanionic σ-bonded ligand that undergoes hydrogenolysis in the presence of hydrogen or hydrosilane;
M is a late first row transition metal;
n equals 2 to 4;
m equals 0 to 4 up to a maximum value of n;
Y is a weakly-coordinating or non-coordinating counter-ion, of formal negative charge 'd', and with stoichiometry 'e' such that d·e=m, and the charge of the counter-ion(s) offsets that of the cluster;
$R_3PN$ is an anionic phosphoranimide ligand of structure:

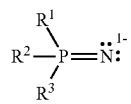

where: $R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group containing at least one heteroatom selected from the group consisting of a Group 15 and Group 16 element, and silicon; $R^1$, $R^2$, $R^3$ may also be linked to give cyclic systems, using linkages such as aliphatic cyclic systems; and wherein the M to R3PN⁻ ratio is 1:1,
the method comprising:
reacting a compound of Formula II: $[A-M(NPR_3)]_n$ wherein A, M, n and $NPR_3$ are defined as in the compound of Formula I with an outer sphere oxidant.

24. The method of claim 23, wherein outer sphere oxidant is a ferrocenium, silver(I), copper(II), Fe(III), or Ce(IV) salt), $[IrCl_6]_2^-$, $[PtCl_6]_2^-$, $[Ni(tfd)_2]$, $[Mo(tfd)_3]$), a halogen, a nitrosonium salt, $[N(aryl)_3]^+$, a thianthrene, a trityl salt, a tropylium salt or a quinone derivative.

25. A method of synthesis of a complex of Formula III:

$$[(MNPR_3)_nX_m] \qquad \text{Formula III}$$

where:
m=2 to 4;
n=2 to 4;
M is Fe, Co or Ni;
X can be any halide or pseudohalide;
$R^3PN$ is an anionic phosphoranimide ligand of structure:

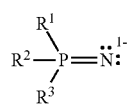

where $R^1$, $R^2$, $R^3$ are the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom, and wherein the substituents may also be linked to give cyclic systems, both aliphatic and aromatic, the method comprising:

conducting an anionic metathesis reaction between a metal salt selected from the group consisting of $MX_m$ and $L_aMX_m$ and an alkali or alkaline metal salt of a phosphoranimide ligand;
wherein:
m on $MX_m$ and $L_aMX_m$=2 to 3;
a=1 to 4;
M is Co, Ni or Fe;
X is a halide or pseudohalide;
L is a two-electron dative donor molecule selected from tetrahydrofuran, 1,2-dimethoxyethane, dioxane a dissociable trialkylphosphine and a triarylphosphine ligand;
and wherein phosphoranimide ligand, $NPR_3$, is defined as in the compound of Formula III.

* * * * *